United States Patent [19]

Hämmerling et al.

[11] 4,446,104
[45] May 1, 1984

[54] APPARATUS FOR TRANSFERRING SAMPLE VESSELS INTO COLLECTING VESSELS

[75] Inventors: Günter Hämmerling, Heidelburg; Ingo Müller, Meckesheim; Erich Menger, Walldorf, all of Fed. Rep. of Germany

[73] Assignee: Deutsches Krebsforschungszentrum, Heidelberg, Fed. Rep. of Germany

[21] Appl. No.: 331,305

[22] Filed: Dec. 16, 1981

[30] Foreign Application Priority Data

Dec. 16, 1980 [DE] Fed. Rep. of Germany ....... 3047265

[51] Int. Cl.³ ..................... G01N 35/04; B65G 47/26; B01L 3/00
[52] U.S. Cl. ..................................... 422/63; 198/424; 414/404; 414/412; 422/50; 422/102; 435/287; 435/300; 436/809
[58] Field of Search ................................. 422/63–67, 422/102, 50; 414/403, 404, 412; 53/247, 255, 263, 320, 321, 322, 313, 539, 521; 198/424; 435/287, 300; 436/809

[56] References Cited

U.S. PATENT DOCUMENTS 3,106,315 10/1963 Bailey ................................... 198/424
3,270,903 9/1966 Willms ................................... 198/424
3,662,518 5/1972 Eisenberg .............................. 53/263

*Primary Examiner*—Michael S. Marcus
*Attorney, Agent, or Firm*—Spencer & Frank

[57] ABSTRACT

A device for transferring sample vessels carried by a microtiter member to collecting vessels which are carried in cassettes and are dimensioned to accommodate the sample vessels. The device is composed of a table provided with a distributor plate for receiving and supporting the microtiter member and which is provided with openings corresponding in number to the number of sample vessels, each opening being located to lie below a respective one of the sample vessels when the microtiter member is supported by the plate; an intermediate plate disposed below the distributor plate and provided with a plurality of openings equal in number to the openings in the distributor plate and each associated with a respective distributor plate opening; a distributor system extending between the distributor plate and the intermediate plate for transferring a respective sample vessel from each distributor plate opening to its associated intermediate plate opening; and a base plate disposed below the intermediate plate for the orderly accommodation of the cassettes in a manner such that each collecting vessel is located below a respective intermediate plate opening.

6 Claims, 4 Drawing Figures

APPARATUS FOR TRANSFERRING SAMPLE VESSELS INTO COLLECTING VESSELS

BACKGROUND OF THE INVENTION

The present invention relates to a device for transferring sample holders, or vessels, disposed at a microtiter plate into collecting vessels having compatible dimensions and disposed in cassettes.

Recently, a series of different testing methods has been developed for the determination of free and cell-bound substances (e.g. proteins), which methods are based on the bond of a suitable radioactively marked indicator (e.g. antibody) with the substance to be determined (=radioimmune test RIA). Of particular interest are modifications of such radioimmuno-chemical processes which make it possible to make hundreds of determinations simultaneously in a short period of time.

In some of these processes the substances to be tested are anchored in recesses of standardized, so-called microtiter plates of a soft plastic, provided with 96 recesses per plate. In this way it is possible to treat 96 samples, or a multiple thereof, simultaneously with a radioactive indicator. Methods of this type are used on a large scale for routine analyses in hospitals and for research, e.g. for the determination of hormones, antibodies, enzymes, metabolites, pharmaceuticals, etc., by solid phase radioimmune testing. In other radioimmune test processes, the sample vessels are individual test tubes which are disposed in a microtiter plate that is used as a stand.

In the prior art, the sample vessels are transferred manually into corresponding counting vessels. For the case where the sample vessels constitute the recesses of microtiter plates, the recesses are severed by means of an electrically heated wire and then are individually transferred into counting vessels by means of forceps, or tweezers. It is also possible to obtain individual recesses with associated stands, but these must be inserted and removed manually. Such products are marketed by the Flow and Dynatech Companies.

Such manual transfer of the sample vessels into counting tubes is a very cumbersome and time-consuming operation. This is a particularly weighty factor because the test procedures are otherwise highly automated so that the above-mentioned process steps constitute a large proportion of the total work time required for these procedures. At the same time there exists the danger of mixups or the loss of samples.

SUMMARY OF THE INVENTION

It is an object of the present invention to provide a device of the above-mentioned type with which sample vessels can be transferred to collecting vessels without mixups, without loss of samples and in a very short time.

The above and other objects are achieved, according to the invention, by the provision of a novel device for automatically transferring sample vessels carried by a microtiter member to collecting vessels which are carried in cassettes and are dimensioned to accommodate the sample vessels. The novel device is composed of: a table provided with a distributor plate for receiving and supporting the microtiter member and which is provided with openings corresponding in number to the number of sample vessels, each opening being located to lie below a respective one of the sample vessels when the microtiter member is supported by the plate; an intermediate plate disposed below the distributor plate and provided with a plurality of openings equal in number to the openings in the distributor plate and each associated with a respective distributor plate opening; means defining a distributor system extending between the distributor plate and the intermediate plate for transferring a respective sample vessel from each distributor plate opening to its associated intermediate plate opening; and a base plate disposed below the intermediate plate for the orderly accommodation of the cassettes in a manner such that each collecting vessel is located below a respective intermediate plate opening.

DESCRIPTION OF THE PREFERRED EMBODIMENTS

Figure 1:
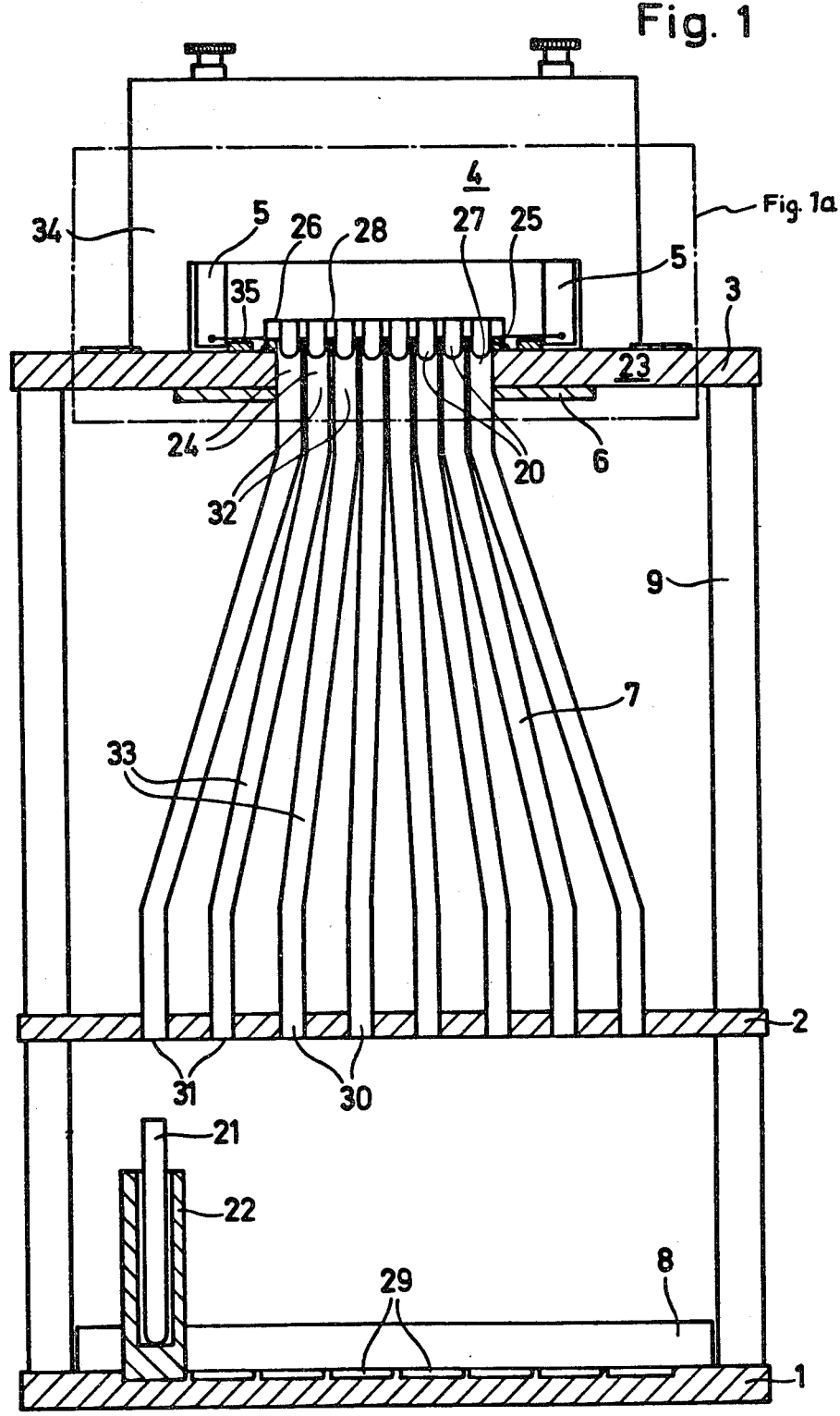
FIG. 1 is an elevational, cross-sectional view of a preferred embodiment of a device according to the invention.
Figure 2:
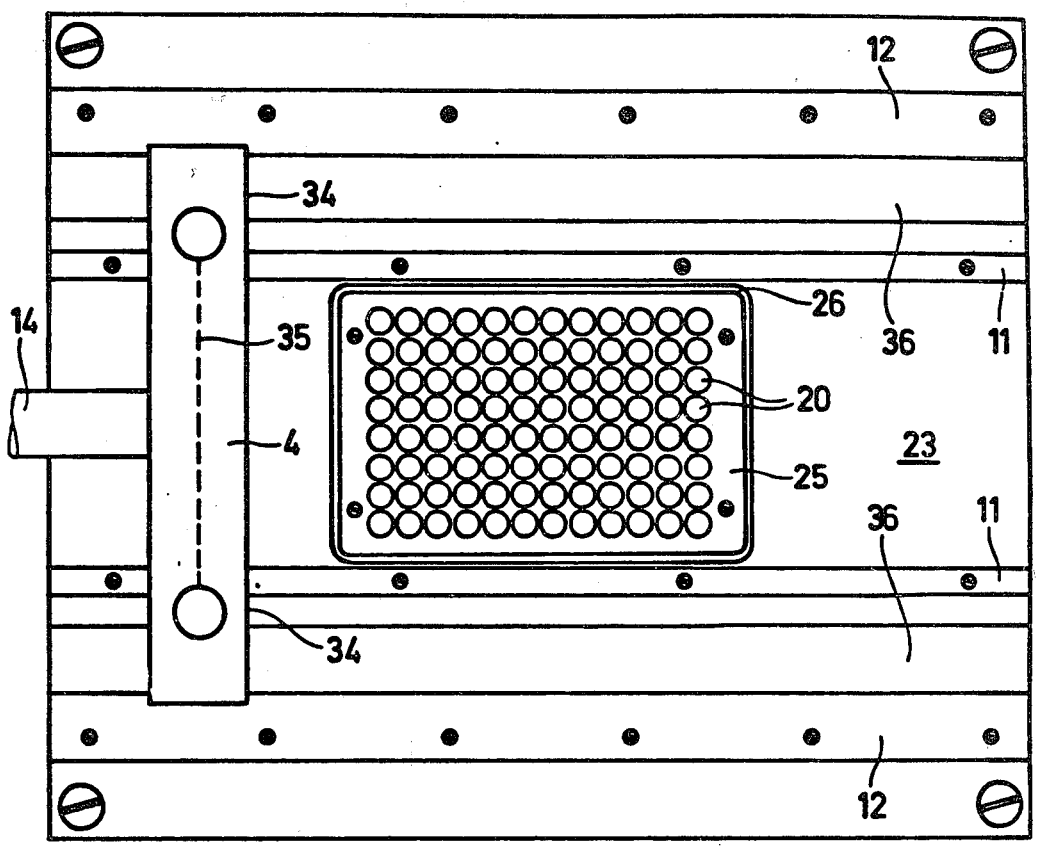
FIG. 2 is a top plan view of the device of FIG. 1.

The device shown in FIGS. 1 and 2 makes it possible, for example, to transfer 96 reaction vessels, or sample vessels, 20 almost simultaneously into collecting vessels 21 which are disposed in respective cassettes 22. Each cassette 22 is associated with a row of such sample vessels 20.

The device includes, inter alia, a table 3 provided with three corner mounts 9. The table 3 includes a table top 23 provided with through bores 24 and a matching distributor plate 25 and receptacle plate 6 through which bores 24 extend.

A microtiter plate 26 of a soft plastic can be placed onto the distributor plate 25 in such a manner that, on the one hand, each associated sample vessel 20 comes to lie above the entrance opening 27 of a respective one of the bores 24. Vessels 20 are associated with a cover plate 28 and when vessels 20 are above openings 27, a certain distance exists between cover plate 28 and the surface of the distributor plate 25. (Flexible microtiter plates M24 of Dynatech Laboratories, USA).

The corner mounts 9 on the table top 23 are seated on a base plate 1 which is provided with mutually parallel grooves 29 to receive and guide the cassettes 22. The position and length of the grooves are dimensioned in such a way that 96 collecting vessels 21, corresponding to the number of sample vessels 20, together with the associated cassettes 22 can be accommodated next to one another. An abutment angle member 8 facilitates the orderly arrangement of the cassettes.

Above the base plate 1 and at a distance above the cassettes 22, an intermediate plate 2 which extends parallel to the table top 23 and to the base plate 1 is fastened to the corner mounts 9. This intermediate plate is also provided with through bores 30 whose cross section and number correspond to the cross section and number of the bores 24 in the table top 23. The lower opening 31 of each bore 30 is disposed above the location provided for a respective collecting vessel 21, when its associated cassette 22 is in position on base plate 1. The spacing between the individual openings 31 is larger, to correspond to the larger dimensions of the cassettes 22, than the corresponding spacing between the lower openings 32 of the bores 24.

The system 7 to distribute the sample vessels 20 to the collecting vessels 21 includes a bundle of pipes the individual pipes 33 of which emanate from the lower openings 32 at the receptacle plate 6 and extend in a straight or curved line to the openings 31 or bores 30 of the intermediate plate 2. Their inner cross sections and their bends are dimensioned in such a way that short as well as long sample vessels 20 can fall through these pipes due to the effect of gravity, with or without the support of compressed air or mechanical means. One example of long sample vessels is shown in FIG. 3.

Figure 1A:
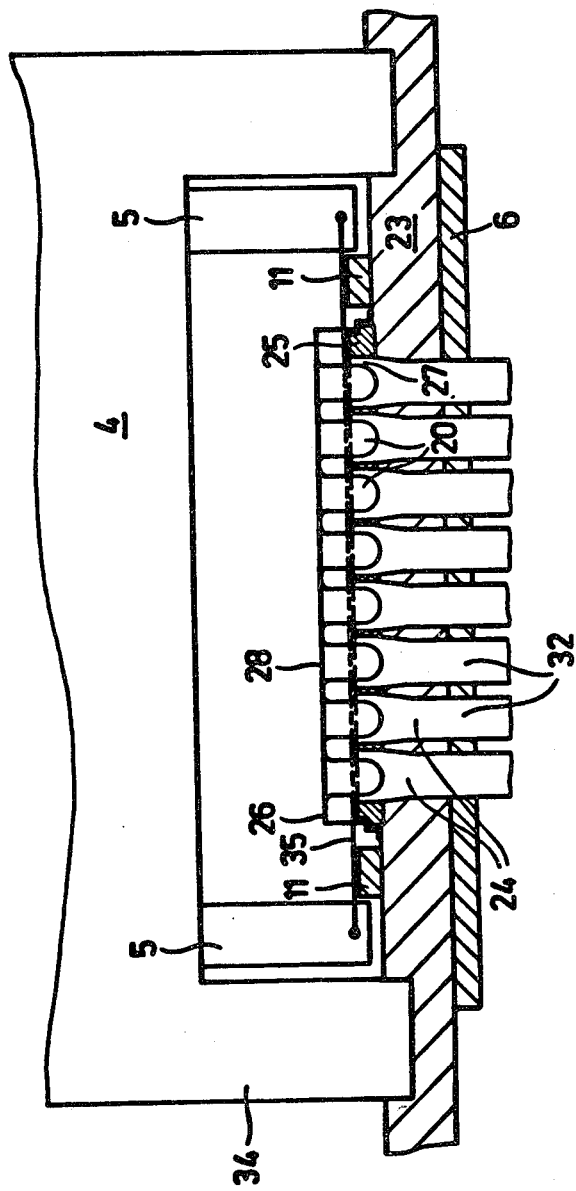
FIG. 1a is an elevational, cross-sectional detail view of the upper portion of the device of FIG. 1.

For the case in which the sample vessels 20 are permanently connected, or integral, with the soft plastic microtiter plate 26, as shown in FIG. 1, the vessels must be severed from the microtiter plate 26 once it has been placed upon the distributor plate 25. A cutting device composed of a carriage 4 with two lateral runners 34 and an electrically heatable cutting wire 35 is provided for this purpose. The cutting wire 35 is tensioned between two electrically insulated wire mounts 5 in such a manner that it can be brought through between the microtiter plate 26 proper and the distributor plate 25 parallel to the surface of the distributor plate 25 at a distance from that surface and from the cover plate 28, as can be best seen in FIG. 1a. During that passage, the wire 35 severs the individual sample vessels 20 by rows from the microtiter plate 26. The sample vessels then fall through the pipes 33 into the respective collecting vessels 21.

FIG. 2 is a top view of the table top 23 with the distributor plate 25 and the microtiter plate 26 holding the sample vessels 20 placed thereon. The carriage 4 may be moved manually by means of a handle 14 along the guide grooves 36 parallel to the longitudinal sides of the distributor plate 25. During this movement, the heated wire 35 severs the sample vessels 20. A spacer strip 11 and a guide strip 12 at both sides of the carriage 4 serve as a guide for the runners 34 of the carriage 4.

Figure 3:
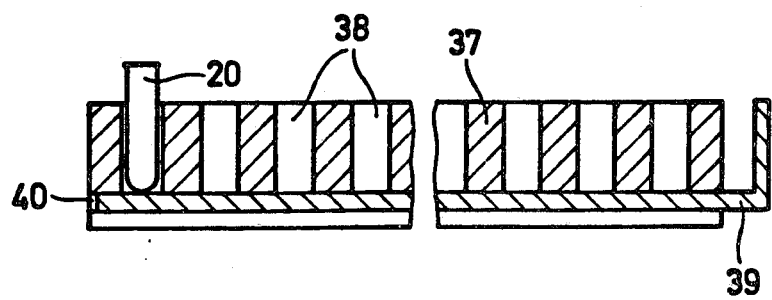
FIG. 3 is a cross-sectional view of a special microtiter plate.

For the case where the individual reaction or sample vessels are isolated test tubes 20', one of which is shown in FIG. 3, the microtiter plate 26 is replaced by a microtiter rack 37. It is provided with the same number of, e.g. 96, through bores 38 to accommodate the sample vessels 20' as did the microtiter plate 26 shown in FIGS. 1 and 2.

The same device as shown in FIG. 1 is used to transfer these comparatively long sample vessels 20' into the collecting vessels 21. However, the cutting device 4, 5, 34, 35 is then not required. In its stead there is provided a slide 39 which is guided in lateral grooves 40 at the underside of the microtiter rack 37. After the rack 37 has been placed onto the distributor plate 25 in such a manner that the bores 38 are aligned with the openings 27 in the distributor plate 25, the slide 39 is pulled out and the sample vessels 20 again fall by rows through the pipes 33 until they reach the collecting vessels 21.

It will be understood that the above description of the present invention is susceptible to various modifications, changes and adaptations, and the same are intended to be comprehended within the meaning and range of equivalents of the appended claims.

What is claimed is:

1. A device for transferring sample vessels permanently connected to a microtiter plate to collecting vessels which are carried in cassettes and are dimensioned to accommodate such sample vessels, comprising:

(a) a table provided with a distributor plate for receiving and supporting such microtiter plate and which is provided with openings corresponding in number to the number of such sample vessels, each opening being located to lie below a respective one of such sample vessels when such microtiter plate is supported by said distributor plate;

(b) an intermediate plate disposed below said distributor plate and provided with a plurality of openings equal in number to said openings in said distributor plate and each associated with a respective distributor plate opening;

(c) means defining a distributor system extending between said distributor plate and said intermediate plate for transferring a respective sample vessel from each distributor plate opening to its associated intermediate plate opening;

(d) a base plate disposed below said intermediate plate for the orderly accommodation of such cassettes in a manner such that each collecting vessel is located below a respective intermediate plate opening;

(e) guide means mounted on said table; and (f) a cutting device which can be moved relative to such microtiter plate, when such microtiter plate is supported by said distributor plate, while being guided by said guide means, for severing such sample vessels from such microtiter plate.

2. Device as defined in claim 1 wherein said distributor system comprises a group of pipes, with each said pipe establishing a connection between one said opening in said distributor plate and an associated opening in said intermediate plate.

3. Device as defined in claim 1 wherein said cutting device comprises a carriage, two holding pins carried by said carriage, a heatable cutting wire tensioned between said holding pins for severing such sample vessels from such microtiter plate when said carriage is being moved.

4. A device as defined in claim 1 wherein said distributor system is constructed for transferring each such sample vessel while maintaining substantially the orientation which each such sample vessel has when connected to such microtiter plate and when such microtiter plate is being supported by said distributor plate.

5. Apparatus for supplying sample vessels to collecting vessels which are carried in cassettes and are dimensioned to accommodate such sample vessels, said apparatus comprising:

(a) a microtiter rack provided with through bores in which such sample vessels are disposed, said rack including a slide member arranged to support such sample vessels and mounted for displacement in grooves to permit such sample vessels to drop out of said through bores;

(b) a table provided with a distributor plate for receiving and supporting said microtiter rack and which is provided with openings corresponding in number to the number of such sample vessels, each opening being located to lie below a respective one of such sample vessels when said microtiter rack is supported by said plate;

(c) an intermediate plate disposed below said distributor plate and provided with a plurality of openings equal in number to said openings in said distributor plate and each associated with a respective distributor plate opening;

(d) means defining a distributor system extending between said distributor plate and said intermediate plate for transferring a respective sample vessel from each distributor plate opening to its associated intermediate plate opening; and (e) a base plate disposed below said intermediate plate for the orderly accommodation of such cassettes in a manner such that each collecting vessel is located below a respective intermediate plate opening.

6. Apparatus as defined in claim 5 wherein said distributor system comprises a group of pipes, with each said pipe establishing a connection between one said opening in said distributor plate and an associated opening in said intermediate plate.

* * * * *